United States Patent [19]

So

[11] Patent Number: 4,570,011

[45] Date of Patent: Feb. 11, 1986

[54] PREPARATION OF CYCLOBUTENE SUBSTITUTED AROMATIC HYDROCARBONS

[75] Inventor: Ying-Hung So, Midland, Mich.

[73] Assignee: The Dow Chemical Company, Midland, Mich.

[21] Appl. No.: 612,164

[22] Filed: May 21, 1984

[51] Int. Cl.$^4$ .............................................. C07C 67/30
[52] U.S. Cl. .................... 560/8; 260/410.5; 260/465 R; 260/465 H; 260/544 B; 560/80; 560/108; 560/139; 562/405; 562/488; 564/153; 564/155; 564/180; 568/734; 568/632; 568/929; 568/930; 570/129; 570/143; 570/183; 585/25; 585/360
[58] Field of Search ............... 260/410.9 R, 465 R, 260/465 H, 544 F, 544 L, 544 P, 410.5, 544 B; 560/1, 8, 80, 108, 139; 562/405, 488; 564/153, 155, 172, 180; 570/129, 143, 182, 183; 568/734, 929, 930; 585/25, 410, 360

[56] References Cited

PUBLICATIONS

Loudon et al, *J. Amer. Chem. Soc.*, 91 (27), 7577 (1969).
Schiess et al, *Tetrahedron Letters*, (46), 4569 (1978).
Boekelheide et al, *Tetrahedron Letters*, (44), 4245 (1978).
Brown, *Pyrolytic Methods in Organic Chemistry*, pp. 105–106, Academic Press, N.Y., N.Y. (1980).
Schiess et al, "A Kinetic Study of Pyrolytic Pathways to Benzocyclobutene", *Tetrahedron Letters*, vol. 23, No. 36, pp. 3665–3668.
Schiess et al, "Formation of Substituted Benzocyclobutenes Through Flash Vacuum Pyrolysis", *Tetrahedron Letters*, vol. 23, No. 36, pp. 3669–3672.
Hussain et al, "Formation of 1-Chlorobenzocyclobutene, Anthracene or Benzofuran by Flash Vacuum Pyrolysis", *Tetrahedron Letters*, vol. 24, No. 6, pp. 609–612.

*Primary Examiner*—Michael L. Shippen
*Attorney, Agent, or Firm*—Norman L. Sims

[57] ABSTRACT

The invention is a process for the preparation of an aromatic hydrocarbon with a cyclobutene ring fused to the aromatic hydrocarbon which comprises, dissolving an ortho alkyl halomethyl aromatic hydrocarbon in an inert solvent and pyrolyzing the solution of ortho alkyl halomethyl aromatic hydrocarbon in the inert solvent under conditions such that the ortho alkyl and halomethyl substituents form a cyclobutene ring thereby forming an aromatic hydrocarbon having a fused cyclobutene ring.

16 Claims, No Drawings

PREPARATION OF CYCLOBUTENE SUBSTITUTED AROMATIC HYDROCARBONS

BACKGROUND OF INVENTION

This invention relates to a process for the preparation of aromatic hydrocarbons with cyclobutene rings fused thereto.

Aromatic hydrocarbons with cyclobutene rings fused thereto are useful in the preparation of monomers, which are useful in the preparation of high performance polymers. These high performance polymers are useful as films, moldable compositions, adhesives, and in the preparation of composites.

Processes for the preparation of aromatic hydrocarbons with cyclobutene rings fused thereto suffer from two major problems. The first problem is that such synthesis involves complex multi-step sequences. Furthermore, some processes result in low yields of the desired product.

What is needed is a process for the preparation of cyclobutene-substituted aromatic hydrocarbons which is simple and results in high yields of said hydrocarbons.

SUMMARY OF INVENTION

The invention is a process for the preparation of an aromatic hydrocarbon with a cyclobutene ring fused to the aromatic hydrocarbon which comprises, dissolving an ortho alkyl halomethyl aromatic hydrocarbon in an inert solvent and pyrolyzing the solution of ortho alkyl halomethyl aromatic hydrocarbon in the inert solvent under conditions such that the ortho alkyl and halomethyl substituents form a cyclobutene ring thereby forming an aromatic hydrocarbon having a fused cyclobutene ring.

This process results in a one-step preparation of cyclobutene-substituted aromatic hydrocarbons in which the hydrocarbons are prepared in high yields.

DETAILED DESCRIPTION OF INVENTION

The starting materials for this process include any aromatic hydrocarbon which has an alkyl group and a halomethyl group ortho to one another. Preferred aromatic hydrocarbons include benzene, naphthalene, phenanthracene, anthracene, biphenyl, binaphthyl, or a diaryl alkane. More preferred aromatic hydrocarbons include benzene, naphthalene, biphenyl, binaphthyl, or a diphenylalkane. The most preferred aromatic hydrocarbon is benzene.

The alkyl substituent on the aromatic hydrocarbon can be any alkyl group, preferably $C_{1-20}$ alkyl, more preferably $C_{1-3}$ alkyl and most preferably methyl. The halomethyl hydrocarbons are preferably bromomethyl or chloromethyl.

The aromatic hydrocarbon can be further substituted with one or more of the following substituents: a carbonyloxyhydrocarbyl, oxycarbonylhydrocarbyl, carboxyamide, carboxy, carbonylhalo, cyano, nitro, hydroxy, hydrocarbyloxy, or halo group. It is preferable that the aromatic hydrocarbon be substituted with one or more of such substituents. Preferred substituents are carbonyloxyhydrocarbyl, oxycarbonylhydrocarbyl, carboxamide, carboxy, carbonylhalo, nitro, or hydrocarbyloxy. More preferred substituents are carbonyloxyhydrocarbyl, oxycarbonylhydrocarbyl, carboxamide or oxyhydrocarbyl. Even more preferred substituents are the carbonyloxyalkyl hydrocarbons with carbonyloxymethyl being most preferred.

In one preferred embodiment wherein the aromatic hydrocarbon is benzene the starting materials correspond to the following formula

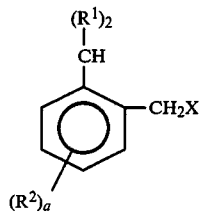

wherein
$R^1$ is separately in each occurrence hydrogen or $C_{1-20}$ alkyl; and
$R^2$ is separately in each occurrence carbonyloxyhydrocarbyl, oxycarbonylhydrocarbyl, carboxamide, carboxylate, carbonylhalo, cyano, nitro, hydroxy, hydrocarbyloxy or halo;
X is chloro or bromo; and
a is an integer of between 0 and 4 inclusive.

Examples of preferred starting reactants include: ortho methylchloromethylbenzene, ortho ethylchloromethylbenzene, ortho propylchloromethylbenzene, ortho butylchloromethylbenzene, ortho pentylchloromethylbenzene, ortho hexylchloromethylbenzene, 3- or 4-methoxy ortho methylchloromethylbenzene, 3- or 4-methoxy ortho ethylchloromethylbenzene, 3- or 4-methoxy ortho propylchloromethylbenzene, 3- or 4-methoxy ortho butylchloromethylbenzene, 3- or 4-ethoxy ortho methylchloromethylbenzene, 3- or 4-ethoxy ortho ethylchloromethylbenzene, 3- or 4-ethoxy ortho propylchloromethylbenzene, 3- or 4-ethoxy ortho butylchloromethylbenzene, 3- or 4-propoxy ortho methylchloromethylbenzene, 3- or 4-propoxy ortho ethylchloromethylbenzene, 3- or 4-propoxy ortho propylchloromethylbenzene, 3- or 4-propoxy ortho butylchloromethylbenzene, 3- or 4-butoxy ortho methylchloromethylbenzene, 3- or 4-butoxy ortho ethylchloromethylbenzene, 3- or 4-butoxy ortho propylchloromethylbenzene, 3- or 4-butoxy ortho butylchloromethylbenzene, 3- or 4-pentoxy ortho methylchloromethylbenzene, 3- or 4-pentoxy ortho ethylchloromethylbenzene, 3- or 4-pentoxy ortho propylchloromethylbenzene, 3- or 4-hexoxy ortho methylchloromethylbenzene, 3- or 4-hexoxy ortho ethylchloromethylbenzene, 3- or 4-hexoxy ortho propylchloromethylbenzene, 3- or 4-hexoxy ortho butylchloromethylbenzene, methyl 3,4-ortho methylchloromethylbenzoate, methyl 3,4-ortho ethylchloromethylbenzoate, methyl 3,4-ortho propylchloromethylbenzoate, methyl 3,4-ortho butylchloromethylbenzoate, ethyl 3,4-ortho methylchloromethylbenzoate, ethyl 3,4-ortho ethylchloromethylbenzoate, ethyl 3,4-ortho propylchloromethylbenzoate, ethyl 3,4-ortho butylchloromethylbenzoate, propyl 3,4-ortho methylchloromethylbenzoate, propyl 3,4-ortho ethylchloromethylbenzoate, propyl 3,4-ortho propylchloromethylbenzoate, propyl 3,4-ortho butylchloromethylbenzoate, butyl 3,4-ortho methylchloromethylbenzoate, butyl 3,4-ortho ethylchloromethylbenzoate, butyl 3,4-ortho propylchloromethylbenzoate, butyl 3,4-ortho butylchloromethylbenzoate, pentyl 3,4-ortho methylchloromethylbenzoate, pentyl 3,4- ortho ethylchloromethylbenzoate, pentyl 3,4-ortho propylchloromethylbenzoate, pentyl 3,4-ortho butylchloromethylbenzoate, hexyl 3,4-ortho methylchloromethylbenzoate, hexyl 3,4-ortho ethylchloromethylbenzoate, hexyl 3,4-ortho propylchloromethylbenzoate, hexyl 3,4-ortho butylchloromethylbenzoate, benzyl 3,4-ortho methylchloromethylbenzoate, benzyl 3,4-ortho ethylchloromethylbenzoate, benzyl 3,4-ortho propylchloromethylbenzoate, benzyl 3,4-ortho butylchloromethylbenzoate, phenyl 3,4-ortho methylchloromethylbenzoate, phenyl 3,4-ortho ethylchloromethylbenzoate, phenyl 3,4-ortho propylchloromethylbenzoate, and phenyl 3,4-ortho butylchloromethylbenzoate.

In one even more preferred embodiment the starting material is methyl 3,4-ortho methylchloromethylbenzoate.

The product prepared by the process of this invention is an aromatic hydrocarbon with a cyclobutene ring fused to one of the rings of the aromatic hydrocarbon. The preferred aromatic hydrocarbons are described hereinbefore. The product can be substituted as described hereinbefore.

In one preferred embodiment, wherein the aromatic hydrocarbon is benzene the products correspond generally to the formula

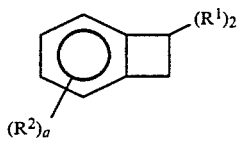

wherein $R^1$, $R^2$ and a are as defined hereinbefore.

Among preferred classes of aromatic hydrocarbons with cyclobutene rings fused thereto include cyclobutabenzene(bicyclo(4.2.0)octa-1,3,5,7-tetraene) 1-alkylcyclobutabenzenes, hydrocarbyl cyclobutabenzoate, hydrocarbyl 1-alkylcyclobutabenzoate, hydrocarboxy cyclobutabenzene, hydrocarboxy 1-alkylcyclobutabenzene, cyclobutabenzamides, and 1-alkylcyclobutabenzamides. Even more preferred classes include alkyl cyclobutabenzoates, cyclobutabenzamides, and alkoxy cyclobutabenzenes.

Examples of some preferred aromatic hydrocarbons with fused cyclobutene rings include methylcyclobutabenzene, ethylcyclobutabenzene, propylcyclobutabenzene, butylcyclobutabenzene, pentylcyclobutabenzene, hexylcyclobutabenzene, benzylcyclobutabenzene, phenylcyclobutabenzene, methyl cyclobutabenzoate, ethyl cyclobutabenzoate, propyl cyclobutabenzoate, butyl cyclobutabenzoate, pentyl cyclobutabenzoate, hexyl cyclobutabenzoate, benzyl cyclobutabenzoate, phenyl cyclobutabenzoate, methoxycyclobutabenzene, ethoxycyclobutabenzene, propoxycyclobutabenzene, butoxycyclobutabenzene, pentoxycyclobutabenzene, hexoxycyclobutabenzene, benzoxycyclobutabenzene, phenoxycyclobutabenzene, N-methylcyclobutabenzamide, N-ethylcyclobutabenzamide, N-propylcyclobutabenzamide, N-butylcyclobutabenzamide, N-pentylcyclobutabenzamide, N-hexylcyclobutabenzamide, N-benzylcyclobutabenzamide, and N-phenylcyclobutabenzamide.

Examples of even more preferred aromatic hydrocarbons with cyclobenzene rings fused thereto are methyl cyclobutabenzoate, ethyl cyclobutabenzoate, propyl cyclobutabenzoate, pentyl cyclobutabenzoate, and hexyl cyclobutabenzoate.

In one of the most preferred embodiments the aromatic hydrocarbon with a cyclobutene ring fused thereto is methyl cyclobutabenzoate.

Hydrocarbyl means herein an organic moiety containing carbon and hydrogen atoms. The term hydrocarbyl includes the following organic moieties: alkyl, alkenyl, alkynyl, cycloalkyl, cycloalkenyl, aryl, aliphatic and cycloaliphatic aralkyl and alkaryl. Aliphatic refers herein to straight- and branched-, and saturated and unsaturated, hydrocarbon chains, that is, alkyl, alkenyl or alkynyl. Cycloaliphatic refers herein to saturated and unsaturated cyclic hydrocarbons, that is cycloalkenyl and cycloalkyl. The term aryl refers herein to biaryl, biphenylyl, phenyl, naphthyl, phenanthranyl, anthranyl and two aryl groups bridged by an alkylene group. Alkaryl refers herein to an alkyl-, alkenyl- or alkynyl-substituted aryl substituent wherein aryl is as defined hereinbefore. Aralkyl means herein an alkyl, alkenyl or alkynyl group substituted with an aryl group, wherein aryl is as defined hereinbefore. $C_{1-20}$ alkyl includes straight- and branched-chain methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl groups.

Cycloalkyl refers to alkyl groups containing one, two, three or more cyclic rings. Cycloalkenyl refers to mono-, di- and polycyclic groups containing one or more double bonds. Cycloalkenyl also refers to cycloalkenyl groups wherein two or more double bonds are present.

Hydrocarbylcarbonyloxy refers to a substituent in which a hydrocarbyl moiety is bonded to a carbonyl moiety which is further bonded to an oxygen atom and includes substituents which correspond to the formula

Hydrocarbylcarbonyl refers herein to a substituent which is a hydrocarbyl moiety bonded to a carbonyl moiety and includes substituents which correspond to the formula

Hydrocarbyloxycarbonyl refers herein to a substituent in which a hydrocarbyl moiety is bonded to an oxygen atom which is further bonded to a carbonyl moiety and includes substituents which correspond to the formula

The term carboxamide refers to a substituent which corresponds to the formula

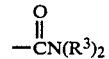

wherein $R^3$ is a hydrocarbyl moiety.

The term carbonylhalo refers to a substituent which corresponds to the formula

wherein X is a halogen.

The term carboxy refers herein to a substituent which corresponds to the formula

The term hydrocarbyloxy refers herein to a substituent which corresponds to the formula

wherein $R^3$ is a hydrocarbyl moiety.

In the process of this invention the ortho alkyl halomethyl aromatic hydrocarbon is dissolved in an inert solvent, and thereafter pyrolyzed to form a cyclobutene ring. Dissolving the aromatic hydrocarbon in a suitable solvent is critical to the invention, as this allows the preparation of the aromatic hydrocarbon with the cyclobutene ring fused thereto in high yields.

In general suitable solvents are those which dissolve the ortho alkyl halomethyl aromatic hydrocarbons and which are stable at pyrolysis conditions. Preferable solvents include benzene, substituted benzenes, biphenyl or substituted biphenyls. Preferred solvents are benzene, toluene, xylene, chlorobenzenes, nitrobenzenes, alkylbenzoates, phenylacetates, or diphenylacetates. The most preferred solvent is xylene.

In general the ratio of solvent to the starting material, the ortho alkyl halomethyl aromatic hydrocarbon, is such that the starting material is dissolved and results in an acceptable yield of products. It is preferable that the ratio of solvents to starting material be at least 2:1. Preferable solvent to starting material ratios are between about 2:1 and 10:1, and 3:1 and 4:1.

During the pyrolysis the starting material dissolved in solvent is exposed to temperatures at which the ortho alkyl halomethyl aromatic hydrocarbon eliminates a hydrogen halide and forms a cyclobutene ring. Suitable temperatures are those at which this takes place. Preferable temperatures are above 550° C. More preferred temperatures are between 550° C. and 750° C., with between about 700° C. and 750° C. being most preferred.

The pyrolysis can take place at any pressure at which good yields of the aromatic hydrocarbons with cyclobutene rings fused thereto are prepared. Preferable pressures are between 760 mm and 5 mm of mercury. More preferred pressures are between 25 mm and 75 mm of mercury, with between about 25 mm and 35 mm of mercury being most preferred.

In one preferred embodiment the pyrolysis takes place by flowing a solution of the ortho alkyl halomethyl aromatic hydrocarbon through a hot tube reactor at the pyrolysis temperatures. In this embodiment it is preferred to pack the hot tube with a packing material. Any packing material which is inert to the reactants and stable to the reaction conditions is suitable, examples include quartz chips and stainless steel helices.

The product can be recovered by distillation of the materials after pyrolysis. In the embodiment wherein a low boiling solvent is used, the solvent comes off in the first cut of a distillation while the product comes off in the second cut. The starting material is usually left as a residual material in the distillation pot and can thereafter be recycled. When high boiling solvents such as biphenyl, substituted biphenyls or diphenylacetates are used, the product is distilled out and the starting material left in the solvent is recycled.

This process generally results in the preparation of cyclobutene fused aromatic hydrocarbons with a yield of about 40 percent, in more preferred embodiments the yield is about 50 percent.

SPECIFIC EMBODIMENTS

The following examples are included for illustrative purposes only, and do not limit the scope of the claims or the invention.

EXAMPLE 1

Pyrolysis of methyl 3-(chloromethyl)-4-methylbenzoate

The experimental setup is a quartz tube packed with quartz chips. The central portion of the tube is placed in a furnace. A 25-centimeter portion of the tube above the furnace serves as a preheating zone and the temperature in the middle of such preheating zone is between about 250° C. and 300° C. Attached to the top of the tube is an addition funnel. Attached to the bottom portion of the tube are cold traps and a means for pulling a vacuum on the tube. Methyl 3-(chloromethyl)-4-methylbenzoate (50 g) is dissolved in 200 g of ortho xylene and placed in the addition funnel. The furnace is heated up to 730° C. A vacuum pump is turned on and pressure is adjusted to 25 mm of mercury. The solution of methyl 3-(chloromethyl)-4-methylbenzoate is added dropwise for a period of 1 hour and 15 minutes. Product and unreacted starting material are collected in cold traps. The pyrolytic tube is flushed with 200 ml of acetone after a cooling down period. The acetone solution is combined with the ortho xylene solution collected in the cold traps. Acetone and ortho xylene are distilled off with a 16-inch Vigreaux column under normal pressure. When most of the ortho xylene is distilled, the system is brought to 0.5 mm mercury and 15.5 g of pure methyl 3,4-cyclobutabenzoate is collected at 61° C. The residue left in the distillation pot is methyl 3-(chloromethyl)-4-methylbenzoate, 23 g.

Experimental Procedure Examples 2-12

A quartz tube packed with quartz chips is placed in an electric furnace such that a 12-cm portion above the furnace serves as a preheating zone, the temperature of which is 250° C. At the top of the quartz tube is inserted an addition funnel. The quartz tube is connected at the bottom to cold traps and a vacuum pump or water aspirator.

A furnace is heated to the desired temperature as indicated by the thermal couple inside a thermal well extended to the middle of the heated zone. Vacuum is then applied. The solution in the addition funnel is then added. The products and unreacted starting material are collected by the cold traps. Product yields are determined by gas chromatography. The material in the addition funnel is the starting material dissolved in ortho xylene or toluene.

EXAMPLES 2–5

In Examples 2–5 the ratio of solvent to starting material is varied. The results are contained in Table I. Table I shows that the pyrolysis of methyl 3-(halomethyl)-4-methylbenzoate using a solvent to starting material ratio of between 21 and 4 results in good selectivity and yield. The selectivity and material balance goes down when the ratio of solvent to starting material is only 2.

TABLE I

| Experiment | Temp (°C.) | Diluent[1] Substrate | Addition[2] Rate ml/min. | Conversion[3] | Selectivity[4] | Yield[5] | Material Balance[6] |
|---|---|---|---|---|---|---|---|
| 2 | 730 | 21.0 | 2.5 | 57 | 79 | 45 | 89 |
| 3 | 725 | 5.5 | 3.0 | 46 | 70 | 32 | 86 |
| 4 | 725 | 4.0 | 3.0 | 45 | 69 | 31 | 88 |
| 5 | 730 | 2.0 | 2.5 | 66 | 55 | 37 | 71 |

[1]Ratio of diluent (solvent) to substrate.
[2]Addition rate of diluent and substrate to the pyrolysis tube.
[3]Conversion refers to the mole percent of reactants converted to products and by-products.
[4]Selectivity refers to the mole percent of the desired product recovered compared to the total products and by-products.
[5]Yield refers herein to mole percent of the desired product compared to the total reactants fed.
[6]Material balance is the mole percent of the unreacted reactant and desired product compared to the total reactants fed to the reactor.

EXAMPLES 6–8

The pressures were varied for the pyrolysis of methyl 3-(halomethyl)-4-methylbenzoate. The results are contained in Table II. Table II demonstrates that lower reaction pressures result in better yields of product.

TABLE II

| Experiment | Pressure (mmHg) | Temp (°C.) | Diluent[1] Substrate | Addition[2] Rate ml/min. | Conversion[3] | Selectivity[4] | Yield[5] | Material Balance[6] |
|---|---|---|---|---|---|---|---|---|
| 6 | 25 | 730 | 21 | 2.5 | 57 | 79 | 45.0 | 89.0 |
| 7 | 150 | 700 | 24 | 2.5 | 51 | 46 | 23.5 | 72.0 |
| 8 | 150 | 715 | 90 | 2.5 | 70 | 40 | 28.0 | 58.5 |

[1]Ratio of diluent (solvent) to substrate.
[2]Addition rate of diluent and substrate to the pyrolysis tube.
[3]Conversion refers to the mole percent of reactants converted to products and by-products.
[4]Selectivity refers to the mole percent of the desired product recovered compared to the total products and by-products.
[5]Yield refers herein to mole percent of the desired product compared to the total reactants fed.
[6]Material balance is the mole percent of the unreacted reactant and desired product compared to the total reactants fed to the reactor.

EXAMPLES 9–12

Pyrolysis of 2-chloromethyl-1-methylbenzene and methyl 3-(halomethyl)-4-methylbenzoate In Examples 9–12, 2-chloromethyl-1-methylbenzene and methyl 3-(halomethyl)-4-methylbenzoate are pyrolyzed. The results are contained in Table III.

TABLE III

| Experiment | Reactant | Temp (°C.) | Pressure (mmHg) | Conversion[1] | Selectivity[2] | Yield[3] | Material Balance[4] |
|---|---|---|---|---|---|---|---|
| 9 | 2-chloromethyl-1-methylbenzene | 710 | 25–35 | 57 | 65 | 37.0 | 80 |
| 10 | methyl 3-(chloromethyl)-4-methylbenzoate | 710 | 25–35 | 42 | 63 | 26.5 | 85 |
| 11 | 2-chloromethyl-1-methylbenzene | 700 | 150–175 | 89 | 34 | 30.0 | 41 |

TABLE III-continued

| Experiment | Reactant | Temp (°C.) | Pressure (mmHg) | Conversion[1] | Selectivity[2] | Yield[3] | Material Balance[4] |
|---|---|---|---|---|---|---|---|
| 12 | 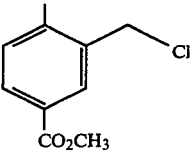 | 700 | 150–175 | 51 | 46 | 23.5 | 72 |

[1]Conversion refers to the mole percent of reactants converted to products and by-products.
[2]Selectivity refers to the mole percent of the desired product recovered compared to the total products and by-products.
[3]Yield refers herein to mole percent of the desired product compared to the total reactants fed.
[4]Material balance is the mole percent of the unreacted reactant and desired product compared to the total reactants fed to the reactor.

What is claimed is:

1. A process for the preparation of an aromatic hydrocarbon with a cyclobutene ring fused to the aromatic hydrocarbon which comprises, dissolving an ortho alkyl halomethyl aromatic hydrocarbon wherein the carbon atom of the ortho alkyl group directly bound to the aromatic ring has at least one hydrogen atom bound to said carbon atom; in an inert solvent and pyrolyzing the solution of ortho alkyl halomethyl aromatic hydrocarbon in the inert solvent under conditions such that the ortho alkyl and halomethyl substituents form a cyclobutene ring thereby forming an aromatic hydrocarbon having a fused cyclobutene ring.

2. The process of claim 1 wherein the weight ratio of solvent to the ortho alkyl halomethyl aromatic hydrocarbon is 2:1 or greater.

3. The process of claim 2 wherein the solvent is benzene, a substituted benzene, diphenyl or a substituted diphenyl.

4. The process of claim 3 wherein the solvent is a benzene, toluene, xylene, a chlorobenzene, nitrobenzene, alkyl benzoate, phenylacetate, or diphenylacetate.

5. The process of claim 4 wherein the solvent is xylene.

6. The process of claim 5 wherein the pyrolysis temperature is 550° C. or greater.

7. The process of claim 6 wherein the pyrolysis pressure is between about 10 and 760 mm Hg.

8. The process of claim 7 wherein the pressure is between about 25 and 75 mm Hg.

9. The process of claim 8 wherein the aromatic radical of the substituted aromatic hydrocarbon is benzene, naphthalene, phenanthracene, anthracene, biphenyl, binaphthyl or a diarylalkane.

10. The process of claim 9 wherein the aromatic radical of the substituted aromatic hydrocarbon is benzene, naphthalene, biphenyl, binaphthyl or a diphenylalkane.

11. The process of claim 10 wherein the aromatic radical of the substituted aromatic hydrocarbon is benzene.

12. The process of claim 11 wherein the ortho alkyl halomethyl aromatic hydrocarbon corresponds to the formula

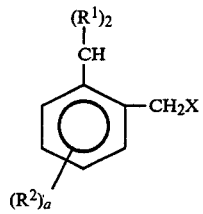

and the aromatic hydrocarbon with a fused cyclobutene ring corresponds to the formula

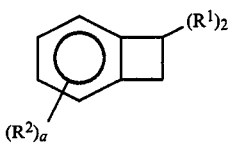

wherein
$R^1$ is separately in each occurrence hydrogen or $C_{1-20}$ alkyl; and
R is separately in each occurrence carbonyloxyhydrocarbyl, oxycarbonylhydrocarbyl, carboxamide, carboxy, carbonylhalo, cyano, nitro, hydroxy, hydrocarbyloxy or halo;
X is chloro or bromo; and
a is an integer of between 0 and 4, inclusive.

13. The process of claim 12 wherein $R^1$ is hydrogen or $C_{1-3}$ alkyl; $R^2$ is carbonyloxyhydrocarbyl, oxycarbonylhydrocarbyl, carboxamide, carboxy, carbonylhalo, nitro or hydrocarbyloxy; X is chlorine; and a is 1.

14. The process of claim 13 wherein $R^1$ is hydrogen; and $R^2$ is carbonyloxyhydrocarbyl, oxycarbonylhydrocarbyl, carboxamide or hydrocarbyloxy.

15. The process of claim 14 wherein $R^2$ is carbonyloxyalkyl.

16. The process of claim 15 wherein $R^2$ is carbonyloxymethyl.

* * * * *

UNITED STATES PATENT AND TRADEMARK OFFICE
CERTIFICATE OF CORRECTION

PATENT NO. : 4,570,011

DATED : February 11, 1986

INVENTOR(S) : YING-HUNG SO

It is certified that error appears in the above-identified patent and that said Letters Patent is hereby corrected as shown below:

Col. 5, line 17, "$R^2$ O" should read --$R^3$ O--.

Col. 10, line 42, "R is" should read -- $R^2$ is --.

Signed and Sealed this

Twenty-first Day of October, 1986

[SEAL]

*Attest:*

DONALD J. QUIGG

*Attesting Officer*     *Commissioner of Patents and Trademarks*